United States Patent [19]
Kim et al.

[11] Patent Number: 5,994,557
[45] Date of Patent: Nov. 30, 1999

[54] METHOD OF ACYLATING AMINES USING N,N'-DIACYLIMIDAZOLONE DERIVATIVES

[75] Inventors: Choong Sup Kim, Seongnam; Ki Seok Cha, Seoul, both of Rep. of Korea

[73] Assignee: Korea Institute of Science and Technology, Seoul, Rep. of Korea

[21] Appl. No.: 09/182,148

[22] Filed: Oct. 29, 1998

[30] Foreign Application Priority Data

Apr. 21, 1998 [KR] Rep. of Korea ................ 98/14170

[51] Int. Cl.$^6$ ................................. C07B 41/06
[52] U.S. Cl. ................... 548/306.4; 548/306.7; 548/309.4; 548/307.1
[58] Field of Search ............... 548/306.4, 309.4

[56] References Cited

U.S. PATENT DOCUMENTS 3,775,333 11/1973 Loffelman et al. ................ 252/99
4,074,046 2/1978 Mohan ................................ 542/439
5,371,185 12/1994 Belleau et al. ..................... 530/326

FOREIGN PATENT DOCUMENTS 1152531 5/1969 United Kingdom ............. 548/306.4

OTHER PUBLICATIONS

Tetrahedron Lett., 22, 1981, 1257–1258 Kunieda et al.
Tetrahedron Lett., 21, 1980, 841–844 Nagao et al.
Tetrahedron Lett., 38, 1997, 3751–3754, Murakami et al.

*Primary Examiner*—Floyd D. Higel
*Attorney, Agent, or Firm*—Darby & Darby

[57] ABSTRACT

The present invention provides a method of acylating organic amines using N,N'-diacylimidazolone derivatives represented by the general formula I as follows:

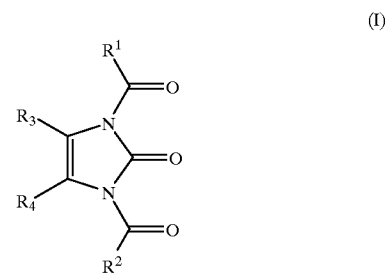

(I)

wherein $R_1$ and $R_2$ are the same or different, which are selected from the group consisting of methyl, ethyl, straight or substituted aliphatic chain of $C_3$–$C_{19}$, phenyl, heterocyclic groups, alkoxy and other organic acid substituting groups; and $R_3$ and $R_4$ are the same or different, which are selected from the group consisting hydrogen, methyl or ethyl, phenyl, substituted phenyl and alkoxycarbonyl, or wherein $R_3$ and $R_4$ form a R-substituted benzene ring having the following structure together with a carbon atom where $R_3$ and $R_4$ are bonded to:

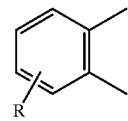

(wherein R is hydrogen, carboxyl or sulfonic groups).

7 Claims, No Drawings

METHOD OF ACYLATING AMINES USING N,N'-DIACYLIMIDAZOLONE DERIVATIVES

BACKGROUND OF THE INVENTION

1. Field of the Invention

The present invention refers to a new acylating method of transforming primary or secondary organic amines into corresponding acyl compounds conveniently by using 1,3-dihydro-1,3-diacyl-1H-benzimidazole-2-one derivatives. Especially, this method showed good regioselectivity in case of diamino compounds where primary and secondary amino group coexist in the same molecule. Two amino groups of diamino compounds which experience different steric or chemical environment showed different reactivities toward this present acylating agent. So it is possible to transfer acyl groups selectively in these diamino system.

2. Description of the Related Art

Until now, N,N'-diacylimidazolone derivatives were presented in U.S. Pat. No. 3,775,333, 1973, as a bleaching activator, but no one has reported the derivatives as an useful acylating agent until the present invention.

The traditional methods for transforming organic amines into acyl compounds were by using acid halide or acid anhydride as acylating agents. However, there are shortcomings, an additional step is required to remove the hydrogen halide or carboxylic acid which is liberated after the reaction. In some cases, the reagent itself which was used to remove the hydrogen halide or carboxylic acid affected the acylated compound or caused difficulties in the purification of the final product.

Where two amines with different steric hindrance and reactivity coexist within one molecule, it is nearly impossible to achieve a selective acylation by using such an acylating agent. For instance, it is rarely possible to acylate a specific amine selectively by using hydrogen halide or acid anhydrides where aminobenzilamine or diamino compounds which have primary and secondary amino groups, or where amines that have structurally different reactivity or steric hindrane. hindrance.

Accordingly, many acylating agents has been reported as candidates of selective acylating agents in a large number of publications and patents. Representative examples are N-acylimidazole (Fieser & Fieser, Organic Reagents), 3-acyl-2-oxazolone (*Tetrahedron Lett.*, 22, 1981, 1257–1258), 3-acythiazol-2-thione (*Tetrahedron Lett.*, 21,1980, 841–844) and N,N-diacetylaniline (*Tetrahedron Lett.* 38, 1997, 3751–3754). However, the selectivity of the acylation reactions is limited to these acylating agents, and it is difficult to purify the products, and it is restricted to transfer only one amine.

SUMMARY OF THE INVENTION

The present invention provides a method of using 1,3-dihydro -1,3-diacyl-1H-benzimidazole-2-one derivatives as an acylating agent. Therfore, it is an object of the present invention to devise acylating agents which facilitate the acylation reaction of amines and the recovery of products; and selectively acylate the specific amines which is less sterically congested; and to substitute simultaneously different groups having different structure. It is another object of the present invention to produce acylating agents which can selectively acylate amino groups in amino acids and amino alcohols.

DETAILED DESCRIPTION OF THE INVENTION

The present invention describes a method of acylating an organic amines using N,N'-diacylimidazolone derivatives represented by the general formula I as follows:

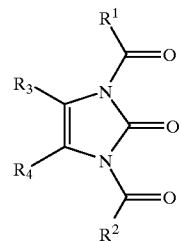

(I)

wherein $R_1$ and $R_2$ are the same or different, which are selected from the group consisting of methyl, ethyl, straight or substituted aliphatic chain of $C_3$–$C_{19}$, phenyl, heterocyclic groups, alkoxy and other organic acid substituting groups; and $R_3$ and $R_4$ are the same or different, which are selected from the group consisting of hydrogen, methyl or ethyl, phenyl, substituted phenyl and alkoxycarbonyl, or wherein $R_3$ and $R_4$ form a R-substituted benzene ring having the following structure, together with the carbon atom where $R_3$ and $R_4$ are bonded to:

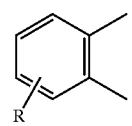

(Wherein R is hydrogen, carboxyl or sulfonic acid groups).

The present invention also provides a new compound represented by the general formula II as follows, among the N,N'-diacylimidazolone derivatives where $R_3$ and $R_4$ form the R-substituted benzene ring together with the carbon atom which they are bonded to:

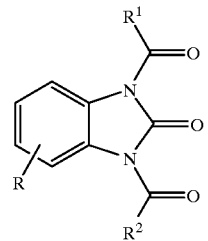

(II)

wherein $R_1$ and $R_2$ are the same as in general formula I, and R is carboxyl or sulfonic acid groups.

The present invention can simultaneously introduce two different amines into one molecule having at least two amines by using N,N'-diacylimidazolone which have different substituted groups $R_1$ and $R_2$ in the general formula I. In case of the acyl groups of the N,N'-diacylimidazolone derivatives of the general formula I are identical, the first transfer of the acyl group is faster than the second one. Where two different acyl groups, however, the $R_1$ is more electro-withdrawing substitution in which the nucleophilicity may be derived from this factor, transfers before the other acyl group. For instance, in general, aromatic acyl group transfers faster than the aliphatic acyl group. As above, acylating of amines can be performed selectively by using the differences in the reactivity of the two different amines.

Also, in case where the primary and secondary amino groups coexist in one reactant amine, selective transfer of the primary amino group can be done at a low reaction temperature (ca. 0° C.). A primary amine or amine with a less steric demand can be acylated among the primary and secondary amines or the amines with a different steric hindrances, respectively. By using similar properties, the amine or amino groups can be acylated with a high selectivity in the amines that have aromatic or aliphatic amino groups in the same or in different compounds.

Accordingly, as stated above, by selecting $R_1$ and $R_2$ in the N,N'-diacylimimidazolone derivatives, desirable acyl groups can be substituted depending on the amine or amino groups in the compounds. For instance, among the N,N'-diacylimidazolone derivatives of the general formula I wherein $R_3$ and $R_4$ form the R-substituted benzene ring together with the carbon atom where $R_3$ and $R_4$ are bonded to, the compound where $R_1$ is methyl and $R_2$ is phenyl can be used as an acylating agent and reacted with 4-aminobenzylamine. At a low reaction temperature, benzoyl group transfers first into the more reactive benzylamino group. When the reaction temperature is raised to refluxing temperature, by substituting the acetyl groups to the aromatic amino groups, different acyl groups such as benzoyl and acetyl can be substituted simultaneously. Also, in the amino alcohol or amino acid, only the amino group can be selectively acylated Meanwhile, whereas most of the compounds represented by the general formula I, except those where R is carboxyl or sulfonic acid groups, have a high solubility in conventional organic solvents, the resultant imidazolones that loses one or both acyl groups as leaving groups have low solubility in water or most of the organic solvent, therefore, from this difference in the solubilities, the resultant acylated amine that is dissolved in the solvent can easily be obtained by removing the produced imidazolones by simple filtration. Moreover, since N,N'-diacylimidazolone derivatives of the general formula II wherein R is carboxyl or sulfonic acid, and the compounds that loses acyl groups as leaving groups from these compounds give high solubility in water, the acylation reaction can be performed in an aqueous environment for the water soluble amines and amino acids.

Most of the acylating agents of the present invention can be synthesized by using the method in U.S. Pat. No. 3,775, 333 (1973) and incorporated as a reference. The compounds that have different $R_1$ and $R_2$ can be obtained by reacting the respective monoacyl compound with an acid chloride that can generate a desired acyl group.

However, N,N'-diacylimidazolone derivatives of the general formula II wherein R is carboxyl or sulfonic acid group are new compounds that are synthesized by the present invention. These compounds can be synthesized easily by reacting with the acid anhydride that can produce the desired acyl group after obtaining the sulfonated compound with a high yield by reacting 2-benzimidazolone with concentrated sulfonic acid.

In the acylation reaction of the present invention, the amount of the N,N'-diacylimidazolone derivatives can be determined by controlling the molar ratio depending on the number of substituting amines. For instance, as shown in formula I, since there are two acyl substituting groups $R_1$ and $R_2$ in one molecule of the N,N'-diacylimidazolone derivatives of the present invention, the molar ratio between the amine compound and the acylating agent of the present invention can be 2:1 for the reaction. However, when two different amino groups are acylated simultaneously with a different $R_1$ and $R_2$, 1:1 molar ratio can be used. Furthermore, when only the amino group with an excellent reactivity is selectively acylated, 1:1 molar ratio can be used since only one acyl group is transferred from the acylating agent of the present invention.

In the acylating of the present invention, generally used organic solvents may be selected as a reaction solvent. Representatively, alcohols such as methanol or ethanol, ethers such as diethyl ether or tetrahydrofuran, dichloromethane, benzene or toluene, and preferably, tetrahydrofuran or dichloromethane can be used as a solvent. Alternatively, for the acylating reaction with the compounds represented by the general formula I wherein R is carboxyl or sulfonic acid groups, water may also be used as a solvent.

The acylation reaction of the present invention can be performed at a wide reaction temperature ranging from $-40°$ C. to $1008°$ C. and can be changed depending on the reaction solvent.

In the acylating of the present invention, reaction conditions can be changed depending on the reacting amines and the object of the acylation since the steric hindrance and reactivity of the amino group to be acylated and the substituted acyl groups, the amount of the acylating agent, reaction time or temperature can all affect the selectivity of the acyl group transfer.

The acylated amines after the acylation reaction according to the present invention can be purified by a further recrystallization. In this case, the solvent can vary depending on the produce acylated amines. Most of the conventional solvents can be used such as hexane, ether, benzene or toluene.

The present invention will be described further in the following examples. These examples are intended for illustrative purposes, and are not intended to limit the scope of the present invention.

EXAMPLE 1

Acylation of Aliphatic Amines

After dissolving 0.01 mole of 1,3-dihydro-1,3-diacetyl-1H-benzimidazol-2-one in 20 mL of dichloromethane, 0.02 mole of aliphatic amines as represented in Table 1 were added and stirred for 30 minutes at room temperature. After the reaction, the produced 2-benzimidazolone was removed by filtration. The solvent was evaporated in vacuo to obtain an acetylated compound almost quantitatively with a higher than 98% yield.

TABLE 1

| Amine | Product | Reaction temperature (° C.) | Reaction time (min) | Yield (%) |
|---|---|---|---|---|
| $CH_3NH_2$ | $CH_3NHAc$ | r.t. | 30 | 98 |
| 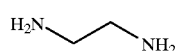 | 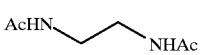 | r.t. | 30 | 98 |

TABLE 1-continued

| Amine | Product | Reaction temperature (° C.) | Reaction time (min) | Yield (%) |
|---|---|---|---|---|
| PhCH₂NH₂ | PhCH₂NHAc | r.t. | 30 | 98 |

EXAMPLE 2
Acylation of Aromatic Amines

After dissolving 0.01 mole of 1,3-dihydro-1,3-diacetyl-1H-benzimidazol-2-one (R=H) in 20 mL of dichloromethane, 0.02 mole of aromatic amines as represented in Table 2 were added and refluxed for 10 hours. After cooling the reaction mixture to room temperature, the precipitate was removed by filtration. The solvent was evaporated in vacuo to obtain the acetylated compound almost quantitatively as in Example 1.

EXAMPLE 3
Selective Acylation of Amines

After dissolving 0.01 mole of 1,3-dihydro-1,3-diacetyl-1H-benzimidazol-2-one in 20 mL of dichloromethane, 0.01 mole of amines as represented in Table 3 were added and reacted by using the reaction times and temperatures as shown in Table 3.

The reaction mixture was heated and refluxed until the reaction was completely evaporated the flask allowed to cool down to room temperatures. And then, resultant precipitation, 2-benzimidazolone, was removed by simple filtration. The solvent was evaporated to obtain the selectively acetylated compound with a higher than 95% yield.

TABLE 2

| Amine | Product | Reaction temperature (° C.) | Reaction time (h) | Yield (%) |
|---|---|---|---|---|
| aniline (PhNH₂) | acetanilide (PhNHAc) | reflux | 10 | 93 |
| 3-methylaniline | 3-methylacetanilide | reflux | 10 | 95 |
| 4-hydroxyaniline | 4-hydroxyacetanilide | reflux | 10 | 94 |

TABLE 3

| Amine | Product | Reaction temperature (° C.) | Reaction time (h) | Yield (%) |
|---|---|---|---|---|
| 4-aminobenzylamine (H₂N-C₆H₄-CH₂NH₂) | 4-amino-N-acetylbenzylamine (H₂N-C₆H₄-CH₂NHAc) | reflux | 15 | 97 |
| N-phenylethylenediamine (PhNH-CH₂CH₂NH₂) | N-phenyl-N'-acetylethylenediamine (PhNH-CH₂CH₂NHAc) | reflux | 12 | 96 |

TABLE 3-continued

| Amine | Product | Reaction temperature (° C.) | Reaction time (h) | Yield (%) |
|---|---|---|---|---|
| H₃CO-indole-CH₂CH₂NH₂ | H₃CO-indoline-CH₂CH₂NHAc | reflux | 12 | 93 |
| H₂N-C₆H₄-NH(Ph) | AcHN-C₆H₄-NH(Ph) | reflux | 12 | 95 |
| 2,6-dimethylpiperazine (NH) | 2,6-dimethyl-N-acetylpiperazine | reflux | 6 | 95 |
| C(CH₃)₂(NH₂)CH₂NH₂ | C(CH₃)₂(NH₂)CH₂NHAc | r.t. | 7 | 95 |
| iPr-NH-CH₂CH₂-NH₂ | iPr-NH-CH₂CH₂-NHAc | r.t. | 6 | 97 |
| HOCH₂CH₂-NH-CH₂CH₂-NH₂ | HOCH₂CH₂-NH-CH₂CH₂-NHAc | r.t. | 6 | 94 |
| Et-NH-CH₂CH₂-NH₂ | Et-NH-CH₂CH₂-NHAc | r.t. | 5 | 96 |

EXAMPLE 4
Acylation of Amino Group in the Amino Alcohols

After adding 1.86 g (0.01 mole) of 1,3-dihydro-1,3-diacetyl-1H-benzimidazol-2-one ($R_1=R_2=CH_3$, $R_3$ and $R_4$ form the R-substituted benzene ring together with the carbon atom where $R_3$ and $R_4$ are bonded to, and R=H) and 1.22 g (0.02 mole) ethanolamine to 30 mL of dichloromethane, reaction was preformed for 5 hours at room temperatures. After the completion of the reaction, the solution was cooled to below 0° C. to solidify the benzimidazolinone which was further removed by filtration. The solvent was evaporated in vacuo to obtain N-acetylethanoleamine with a higher to than 95% yield.

EXAMPLE 5
Simultaneous Acylation of 4-Aminobenzylamine with Different Acyl Groups After dissolving 2.8 g (0.01 mole) of 1,3-dihydro-1-acetyl-3-benzoyl-1H-benzimimidazol-2-one ($R_1=C_6H_5$, $R_2=CH_3$, $R_3$ and $R_4$ form the R-substituted benzene ring together with the carbon atom where $R_3$ and $R_4$ are bonded to, and R=H) in 50 mL of tetrahydrofuran and lowering the reaction temperature to below −30° C., 1.2 g (0.01 mole) of 4-aminobenzylamine was added, and the solution was stirred at this temperature for 2 hours. The reaction mixture was heated and refluxed for 12 hours. After the completion of the reaction, the solution was cooled to room temperature, and the solvent was evaporated in vacuo. The solid that was formed after adding 20 mL of methylene chloride was filtered out. After the solvent was evaporated, the solid was filtered by adding hexane to obtain 2.3 g of N-[4-(acetamido)benzyl] benzamide (m.p.: 175–177° C., 85%).

EXAMPLE 6
Simultaneous Acylation of Piperazine with Different Acyl Groups

After dissolving 2.8 g (0.01 mole) of 1,3-dihydro-1-acetyl-3-benzoyl-1H-benzimidazol-2-one ($R_1=C_6H_5$, $R_2=CH_3$, $R_3$ and $R_4$ form the R-substituted benzene ring together with the carbon atom where $R_3$ and $R_4$ are bonded to, and R=H) in 50 mL of tetrahydrofuran and lowering the reaction temperature to below −40° C., 0.9 g (0.01 mole) of piperazine was added, and the solution was stirred at this temperature for 2 hours. The reaction mixture was heated and refluxed for 24 hours. After the completion of the reaction, the solution was cooled to room temperature, and the solvent was evaporated in vacuo. To the remaining material, 20 mL of dichloromethane was added and stirred at room temperatures. After filtering out the precipitation and evaporating the solvent, 2.0 g of 1-acetyl-4-benzoylpiperazine was obtained by recrystallization.

EXAMPLE 7
N-Acylation of Glycine

After dissolving 2.66 g (0.01 mole) of 1,3-dihydro-1,3-diacetyl-1H-benzimidazol-2-one-5-sulfonic acid ($R_1=R_2=CH_3$, $R=SO_3H$) and 1.5 g (0.02 mole) of glycine in 30 mL of water, the mixture was stirred for 5 hours at room temperatures. Most of N-acylglycine that precipitate out was obtained by filtration. The dissolved portion was extracted with an organic solvent and the solvent was evaporated in vacuo to obtain N-acylglycine almost quantitatively.

EXAMPLE 8
Preparation of 1,3-dihydro-2H-benzimidazol-2-one-5-sulfonic Acid

After dissolving 67 g (0.5 mole) of 1,3-dihydro-1H-benzimidazol-2-one in 100 mL of concentrated sulfuric acid at room temperatures, the mixture was stirred for 7 hours at 100° C. After the completion of the reaction, the reaction mixture was cooled to room temperature, and subsequently added with ice-cold water, it was neutralized to pH 6.0 by adding 50% sodium hydroxide aqueous solution. The produced crystals were filtered, washed with acetone and dried to obtain 96 g (90% of theoretical yield) of 1,3-dihydro-1H-benzimidazol-2-one-5-sulfonic acid.

m.p.: 267–270° C.; NMR (300 MHz, DMSO-$d_6$): δ10.60 (bs, 1H), 10.57 (bs, 1H), 7.22 (d, J=7.4 Hz, 1H), 7.17 (s, 1H), 6.82 (d, J=8.0 Hz, 1H); IR(KBr): 624, 1092, 1174,1216, 1702, 3192, 3410 cm$^{-1}$

Preparation of 1,3-dihydro- 1,3-diacetyl-2H-benzimidazol-2-one-5-sulfonic acid

After suspending the 1,3-dihydro-1H-benzimidazol-2-one-5-sulfonic acid obtained above in 1 L of acetic anhydride and adding 2 g of dimethylamidopyridine, the mixture was reacted for 24 hours by heating it at 95–100° C. After the completion of the reaction, the mixture was cooled to room temperature. The precipitation was filtered, washed with diethylether and dried to obtain 111 g (92% theoretical yield) of 1,3-dihydro-1,3-diacetyl-1H-benzimidazol-2-one-5-sulfonic acid.

m.p.:>280° C.; NMR (300 MHz, $D_2O$): δ8.46 (d, J=2.19 Hz,1H), 8.17 (d, J=8.67 Hz, 1H), 7.73 (dd, J=8.87 Hz, J'=2.39 Hz, 1H), 2.74 (s, 6H); IR(KBr): 652, 1036, 1168, 1226, 1330,1740, 1780 cm$^{-1}$

As described above, the method of using N,N'-diacylimidazolone derivatives as an acylating agent to acylate the organic amines is an effective method of acylating primary or secondary amines. This method can transfer simultaneously the different acyl groups to amino groups having different steric hindrances. The acylation of amino groups can be performed selectively, in a variety of solvents including water even for amines that have alcohol or acid groups. Moreover, the target acylated compounds can be obtained easily since the compounds that lost the acyl as leaving groups from N,N'-diacylimidazolone derivatives can be removed by filtration. Therefore, this method of using N,N'-diacylimidazolone derivatives as an acylating agent have several industrial applications.

Although the preferred embodiments of the present invention have been disclosed for illustrative purposes, those skilled in the art will appreciate that various modifications, additions and substitutions are possible, without departing from the scope and spirit of the invention as recited in the accompanying claims.

What is claimed is:

1. A method of of acylating an organic amine using as an acylating agent an N,N'-diacylimidazolone of formula I;

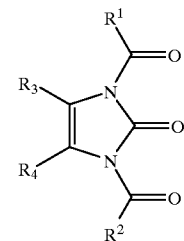

(I)

wherein $R_1$ and $R_2$ are the same or different, which are selected from the group consisting of methyl, ethyl, a straight aliphatic chain of $C_3$–$C_{19}$, a substituted aliphatic chain of $C_3$–$C_{19}$, phenyl, heterocyclic groups, and alkoxy groups; and $R_3$ and $R_4$ are the same or different, which are selected from the group consisting of hydrogen, methyl or ethyl, phenyl, substituted phenyl and alkoxycarbonyl, or wherein $R_3$ and $R_4$ form a R-substituted benzene ring having the following structure, together with a carbon atom where $R_3$ and $R_4$ are bonded to:

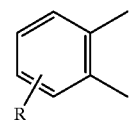

wherein R is hydrogen, carboxyl or sulfonic acid groups.

2. The method according to claim 1, wherein the organic amine consists of a diamine having two or more amino groups.

3. The method according to claim 2, wherein amino groups of the diamine compound are substituted simultaneously with different acyl groups by using the N,N'-diacylimidazolone compounds of the formula I wherein $R_1$ and $R_2$ are different.

4. The method according to claim 1, wherein a primary amine is selectively acylated in a reaction system where primary and secondary amines are the organic amines.

5. The method according to claim 1, wherein an aliphatic amine is selectively acylated in a reaction system where aliphatic and aromatic amines are the organic amines.

6. The method according to claim 1, wherein the R is carboxyl or sulfonic acid groups.

7. An N,N'-diacylimidazolone compound represented by the formula II as follows:

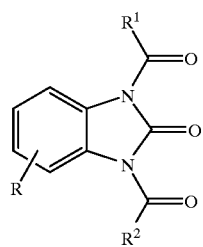
(II)
wherein $R_1$ and $R_2$ are the same or different, which are selected from the groups consisting of methyl, ethyl, a straight aliphatic chain of $C_3$–$C_{19}$, a substituted aliphatic chain of $C_3$–$C_{19}$-phenyl, heterocyclic groups, alkoxy groups; and R is carboxyl or sulfonic acid groups.
* * * * *